United States Patent [19]
Engdahl et al.

[11] Patent Number: 5,345,082
[45] Date of Patent: Sep. 6, 1994

[54] SCINTILLATION CAMERA UTILIZING ENERGY DEPENDENT LINEARITY CORRECTION

[75] Inventors: John C. Engdahl, Columbia, Md.; Michel Pierfitte, Buc, France

[73] Assignee: Sopha Medical Systems, Inc., Columbia, Md.

[21] Appl. No.: 35,088

[22] Filed: Mar. 22, 1993

[51] Int. Cl.$^5$ ............................................. G01T 1/164
[52] U.S. Cl. .......................... 250/363.07; 250/363.09; 364/413.24; 364/571.04
[58] Field of Search ...................... 250/363.07, 363.09; 364/413.24, 571.04

[56] References Cited

U.S. PATENT DOCUMENTS

| | | |
|---|---|---|
| 4,298,944 | 11/1981 | Stoub et al. ................... 250/363.07 |
| 4,316,257 | 2/1982 | Del Medico et al. .......... 250/363.07 |
| 4,323,977 | 4/1982 | Arseneau ........................ 250/363.07 |
| 4,661,909 | 4/1987 | Kumazawa et al. ............ 250/363.07 |

*Primary Examiner*—Carolyn E. Fields
*Attorney, Agent, or Firm*—Rothwell, Figg, Ernst & Kurz

[57] ABSTRACT

A scintillation camera is provided with multiple linearity correction maps which are accessed as a function of the value of the energy of a detected radiation event, so as to separately correct for spatial dislocation errors in multiple energy ranges as a function of detected position. The correction maps may be obtained by direct measurement of nonlinearities for each of the desired energy ranges individually, or sets of corrections for some energy ranges may be obtained by extrapolation calculation from correction factors which have been obtained by direct measurement.

6 Claims, 3 Drawing Sheets

SCINTILLATION CAMERA UTILIZING ENERGY DEPENDENT LINEARITY CORRECTION

BACKGROUND OF THE INVENTION

1. Field of the Invention

The present invention relates generally to imaging devices for nuclear medicine, and more specifically relates to gamma ray or scintillation cameras and methods of correcting images obtained by such cameras for distortions due to nonlinear spatial response of the camera to incident radiation events.

2. Background and Prior Art

In nuclear imaging, a patient is injected with or swallows a radioactive isotope which has an affinity for a particular organ. Gamma rays are then emitted from the organ of interest, and are detected by a gamma ray or scintillation camera device which forms an image of the organ based on the concentration and distribution of the radioactive isotope within the organ.

The scintillation camera as utilized in nuclear medicine is a well known device. The original scintillation camera or "Anger camera" (named after the inventor) is described in U.S. Pat. No. 3,011,057. The Anger camera uses a scintillation crystal, such as a NaI crystal, which absorbs incident gamma rays from the object under study and interacts with the gamma ray to produce light events. An array of photomultiplier tubes is placed adjacent to the crystal in order to detect and amplify these light events so as calculate the spatial location and energy level of the incident gamma ray to produce a two dimensional image of the object which then may be displayed on a CRT or printed as a hard copy.

For each incident gamma ray which interacts with the crystal, the electronic circuitry of the camera combines the output of the photomultiplier tubes and individually computes the spatial (x,y) coordinates and the energy signal (z) for the detected radiation event. An image is generated by plotting the x,y position of a large number (typically millions) of such events. Since cosmic gamma rays and gamma rays which have been scattered will be incident on the detector in addition to incident gamma rays emitted from the radioactive isotope within the organ of interest, the energy signal z is used to identify certain detected gamma rays as being desired for contribution to the image, from among all gamma rays which are incident on the detector. The energy signal z has a functional relationship to the total energy of an incident gamma ray and thus incoming gamma rays are discriminated on the basis of the amplitude of this energy signal.

It is well known in the art that images formed from calculated coordinates of light events detected on the crystal of the camera head contain certain distortions. One such distortion is a spatial dislocation or linearity distortion, in which the coordinates of an event which occurs at a certain location on the crystal will be computed as being at a location which diverges from the true location. This distortion occurs because the calculated position of an incident gamma ray is dependent upon and varies with the location of the light event in the crystal with respect to the photomultiplier tubes. The effect of this is that light events in certain regions of the detector are moved toward the centers of the photomultiplier tubes and thus increasing the apparent density of events, leaving other regions where the perceived density is lower. This creates a so-called "barrel and pincushion" effect which causes an image to have a very nonuniform appearance.

Corrections for such spatial dislocation errors is known in the art and is disclosed in U.S. Pat. No. 4,212,061 to Knoll et al., which is incorporated by reference herein. Spatial coordinate correction factors are typically calculated by presenting a radiation image of a known pattern such as a grid of parallel lines or points, to the gamma camera detector. The spatial coordinates computed by the detector circuitry are then compared with the known coordinates of the grid pattern in order to calculate spatial coordinate correction factors which function to move the computed event positions to the actual, true positions. The calculation of spatial coordinate correction factors is conventionally performed with a gamma camera by utilizing the radioisotope of most common usage. In nuclear medicine, this is typically $^{99m}Tc$ which emits a gamma ray of 140 keV. Additionally, cobalt 57 which emits a gamma ray of 122 keV may be used.

In nuclear medical imaging applications, it is sometimes desired to simultaneously image gamma rays from radioisotopes which emit gammas at more than one energy, or to image gamma rays from two different radioisotopes. Different energy gamma rays produce different numbers of light photons when they are absorbed in the scintillation crystal. The number of light photons produced when a photoelectric absorption of a gamma ray occurs in the crystal is roughly linearly proportional to the energy of the absorbed gamma ray. For example, a gamma ray of 200 keV would produce approximately twice the number of scintillation photons as a gamma ray of 100 keV, assuming each was absorbed in the identical location in the scintillation crystal, and that each was totally absorbed by the photoelectric effect. Small differences occur in the calculated position of events of differing energies due to nonlinearities in the electronic circuitry processing the signals from the photomultiplier tubes generated through absorption of the scintillation photons.

As such, the nonlinearities associated with the spatial coordinate computation of light events are not only dependent on the spatial position of the event in the scintillation crystal, but are also dependent on the energy of the incident gamma ray. Therefore, linearity correction factors obtained for gamma rays of one particular energy will not be identical to correction factors obtained for radioisotopes emitting gamma rays at a different energy absorbed in the same location.

SUMMARY OF THE INVENTION

The present invention overcomes the disadvantages discussed above by providing a scintillation camera which corrects for spatial dislocation errors in the calcuated event positions of absorbed gamma rays in a scintillation detector as a function of energy as well as spatial position in the crystal. The invention improves the uniformity and accuracy of spatial position computation and storage of events of differing energies when those events are acquired over the same period of time.

In particular, the present invention provides a scintillation camera, comprising a camera head including a detector for detecting an incident radiation event, means for computing spatial coordinates corresponding to the location of the detected radiation event, means for developing an energy signal proportional to the energy level of the detected radiation event, means for determining a range of energies into which the energy signal falls and generating a signal corresponding thereto, storage means for storing a plurality of sets of spatial coordinate correction factors, each corresponding to a particular energy range, means for selecting a set of spatial coordinate correction factors from the storage means as a function of the signal from the means for determining, means for retrieving correction factors from the selected set of spatial coordinate correction factors as a function of the computed spatial coordinates, and means for correcting the computed spatial coordinates with the retrieved correction factors.

The present invention further provides a method for correcting spatial coordinates of detected radiation events computed by a scintillation camera, comprising the steps of determining the energy range of a detected radiation event selecting a set of spatial coordinate correction factors as a function of the determined energy range of the detected event, retrieving correction factors from the selected set of spatial coordinate correction factors as a function of the computed spatial coordinates, and correcting the computed spatial coordinates with the retrieved correction factors.

BRIEF DESCRIPTION OF THE DRAWINGS

The present invention will become more fully understood from the detailed description given hereinbelow and the accompanying drawings, which are given by way of illustration only and which are not limitative of the present invention, and wherein.

DETAILED DESCRIPTION OF THE PREFERRED EMBODIMENTS

Figure 1:
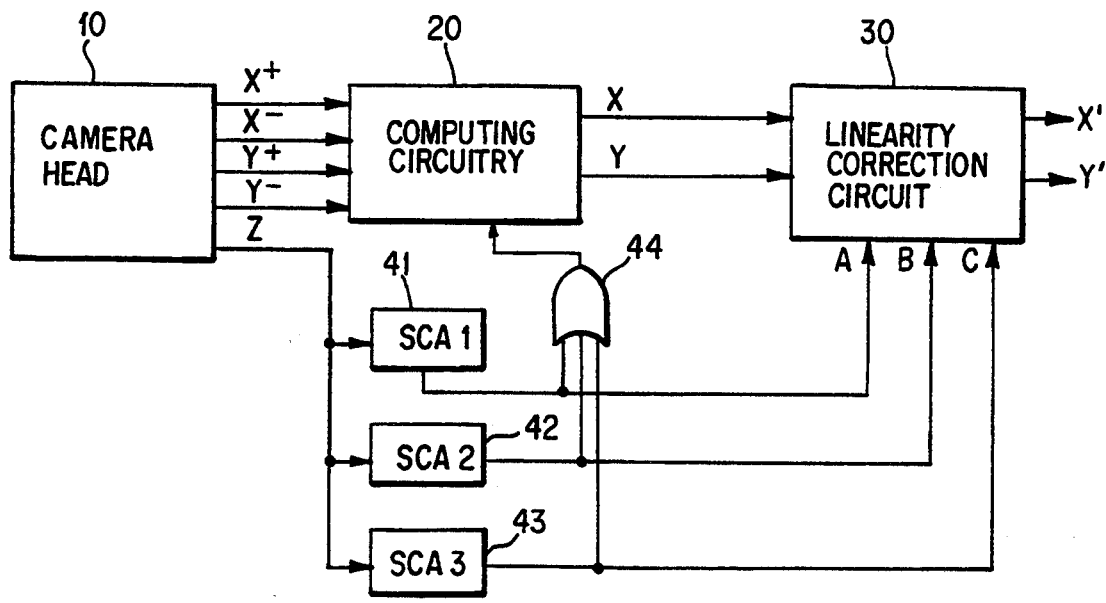
FIG. 1 is a block diagram of a scintillation camera according to the present invention.

FIG. 1 is a block diagram of one preferred embodiment of the novel scintillation camera according to this invention. Camera head 10 represents a conventional gamma camera detector head including a scintillation crystal, photomultiplier tubes and associated resistor matrix circuitry for producing localization signals X+, X−, Y+, and Y−, and an energy signal Z in response to the photoabsorption of an incident gamma ray in the crystal, as conventionally known in the art (see U.S. Pat. No. 3,011,057).

Element 20 represents conventional coordinate computation circuitry which computes spatial coordinates (X, Y) in response to localization signals X+, X−, Y+, and Y− of a detected radiation event of appropriate energy. Element 30 represents a novel linearity correction circuit according to the present invention. The linearity correction circuit receives computed coordinates (X, Y) at input terminals thereof and corrects the computed coordinates to true coordinates (X', Y') which are outputted at output terminals thereof. Elements, 41, 42 and 43 denote single channel analyzers (SCAs), which are conventional logic circuits that output a logic signal when the amplitude of an input signal falls between upper and lower thresholds set in the SCAs. In the present invention, each of SCAs SCA 1, SCA 2, and SCA 3 are set to have upper and lower thresholds of differing values such that the SCAs each define a different, nonoverlapping range of gamma ray energies. The energy signal Z is simultaneously applied to the input terminals of each of the SCAs 41–43. The SCA having an upper and lower threshold within which the energy signal Z falls will produce a logic output signal to linearity correction circuit 30 indicating that the event whose coordinates are being inputted has an energy lying within the range defined by that SCA. The outputs of the SCAs are also applied to a logic circuit, such as OR gate 44, which provides an enable signal to the computing circuitry 20 that instructs the computing circuitry to calculate X, Y coordinates if the energy signal Z lies anywhere within the overall range defined by the SCA settings. It is noted that additional energy discrimination is performed by the camera electronics in order to eliminate spurious events from being counted as part of the resulting image; this is not shown in the drawings or described further in the interest of simplicity, since it is not germane to the concepts of the present invention.

Figure 2:
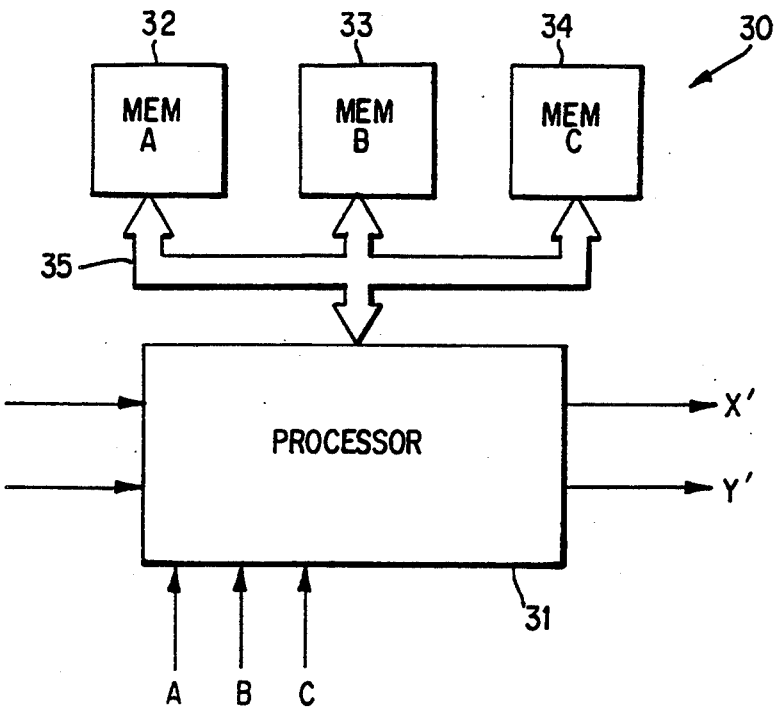
FIG. 2 is schematic block diagram of the linearity correction circuit of FIG. 1 according to one preferred embodiment of the present invention.

A detailed block diagram of the linearity correction circuit 30 is shown in FIG. 2. Processor circuitry 31 receives input coordinates (X, Y), a logic signal A, B or C from one of the SCAs, retrieves correction factors, and outputs corrected coordinates (X', Y') as a function of the input coordinates, logic signal, and correction factors.

According to the present invention, separate sets of spatial coordinate correction factors are stored in memory for events of different energies. This is represented in FIG. 2 by memories 32, 33, and 34 (memories A, B and C, respectively). In other words, for an event having an energy signal within the range set in SCA 1, the processor will receive a logic signal at port A, and thus will select the set of correction factors from memory A over bus 35 for correction of the inputted coordinates from the computing circuitry. Similarly, for events having energy signals within the range set in SCA 2, the processor receives a logic signal at port B and selects the set of correction factors from memory B, and analogously for SCA 3. The three energy ranges might correspond to gamma rays less than 100 keV, between 100 and 200 keV, and above 200 keV, for example. While three energy ranges have been shown, it is apparent that as many energy ranges as desired may be included in the device by merely adding SCAs and associated sets of correction factors. Memories 32, 33 and 34 are illustrated as separate memories only for the purpose of explanation, it being understood and recognized that the memories may be constituted by a single memory having separately addressable sets of correction factors, or any other conventional storage and retrieval expedient.

The linearity correction factors can be obtained by either measuring the nonlinearity of the spatial response of the camera system for each of the energy ranges individually, or the correction factors for one region could be obtained by direct measurement and calculation, and the correction factors for other regions could be extrapolated through calculation from the correction factors from the one region. Techniques for obtaining and calculating linearity correction factors are well known and are described in the aforementioned U.S. Pat. No. 4,212,061. The general behavior of spatial non-linearities as a function of spatial position is predictable as a function of energy. The use of such extrapolation procedures for higher energy ranges in particular would be useful because of the difficulty in obtaining direct measurements of lines or points given the higher penetration depth of the higher energy gamma rays, which would require the use of thicker and heavier lead masks.

Figure 3A:
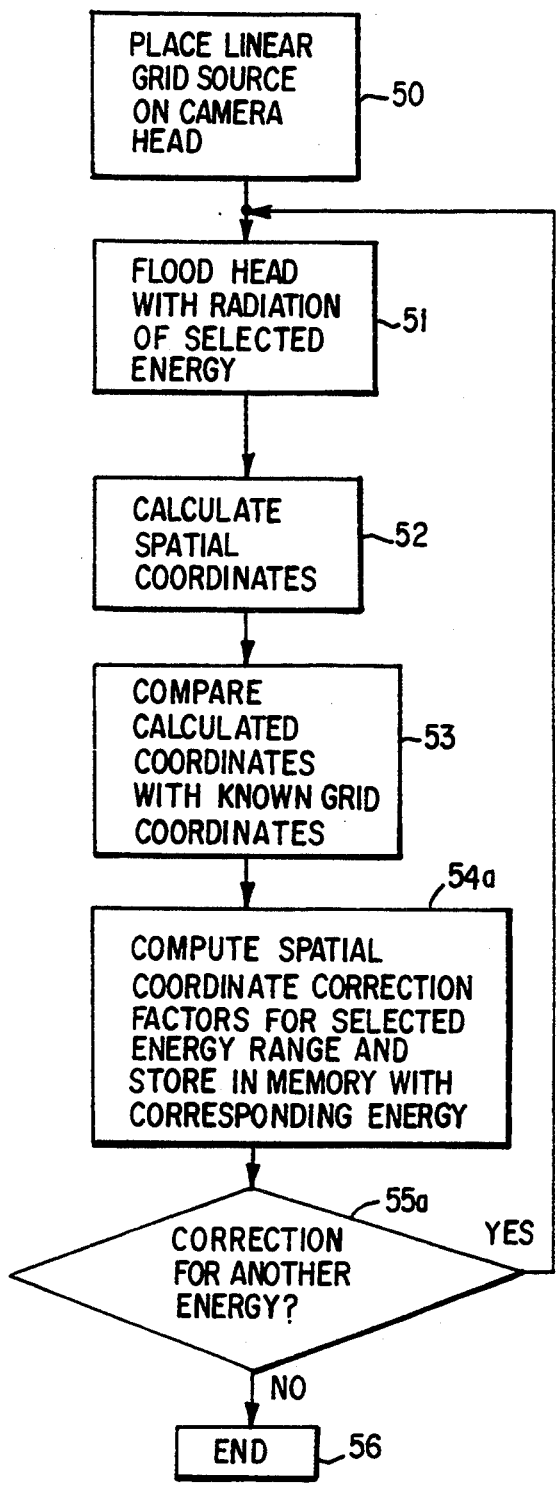
FIGS. 3A and 3B are flow chart diagrams explaining two alternative methods of obtaining spatial coordinate correction factors during a calibration mode of a scintillation camera according to one preferred embodiment of the present invention.
Figure 3B:
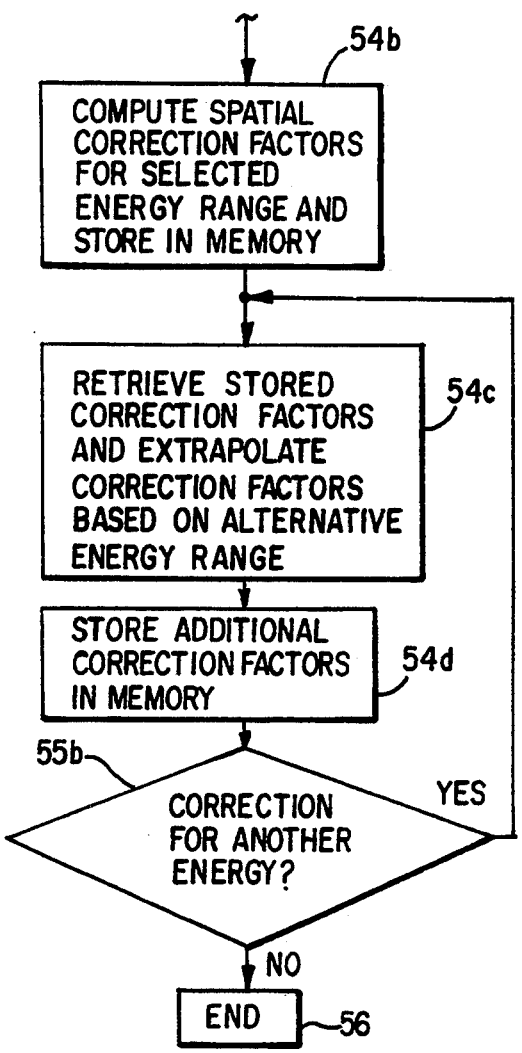

FIGS. 3A and 3B illustrate alternate procedures for obtaining spatial coordinate correction factors according to the present invention. In FIG. 3A, at step 50 a linear grid source, such as parallel lines or points, is placed on the camera head between the head and a uniform source of radiation. At step 51, the head is flooded with this uniform radiation of a selected energy. At step 52, the spatial coordinates of the detected events are computed. These computed coordinates are then compared with the known spatial coordinates of the grid lines or points, at step 53. The spatial coordinate correction factors are then computed based on this comparison, at step 54a, and are stored in memory along with the associated energy range to which they pertain. If correction factors for a different energy range are to be obtained at step 55a, the process returns to step 51 for flooding with a uniform source of the different energy range. If not, the process ends at step 56.

In FIG. 3B, the first three steps are the same as those of FIG. 3A, and are omitted for the sake of simplicity. At step 54b, the spatial correction factors for the source of the selected energy level are computed and stored. At step 54c, correction factors for an alternate energy range are computed by retrieving the stored correction factors obtained from direct measurement and extrapolating correction factors for the alternate energy range through calculation according to the predictive model of behavior. At step 54d, these alternate energy range correction factors are stored in memory. If a set of correction factors is desired for another energy range at step 55b, the process returns to step 54c, and if not, the process ends at step 56.

Figure 4:
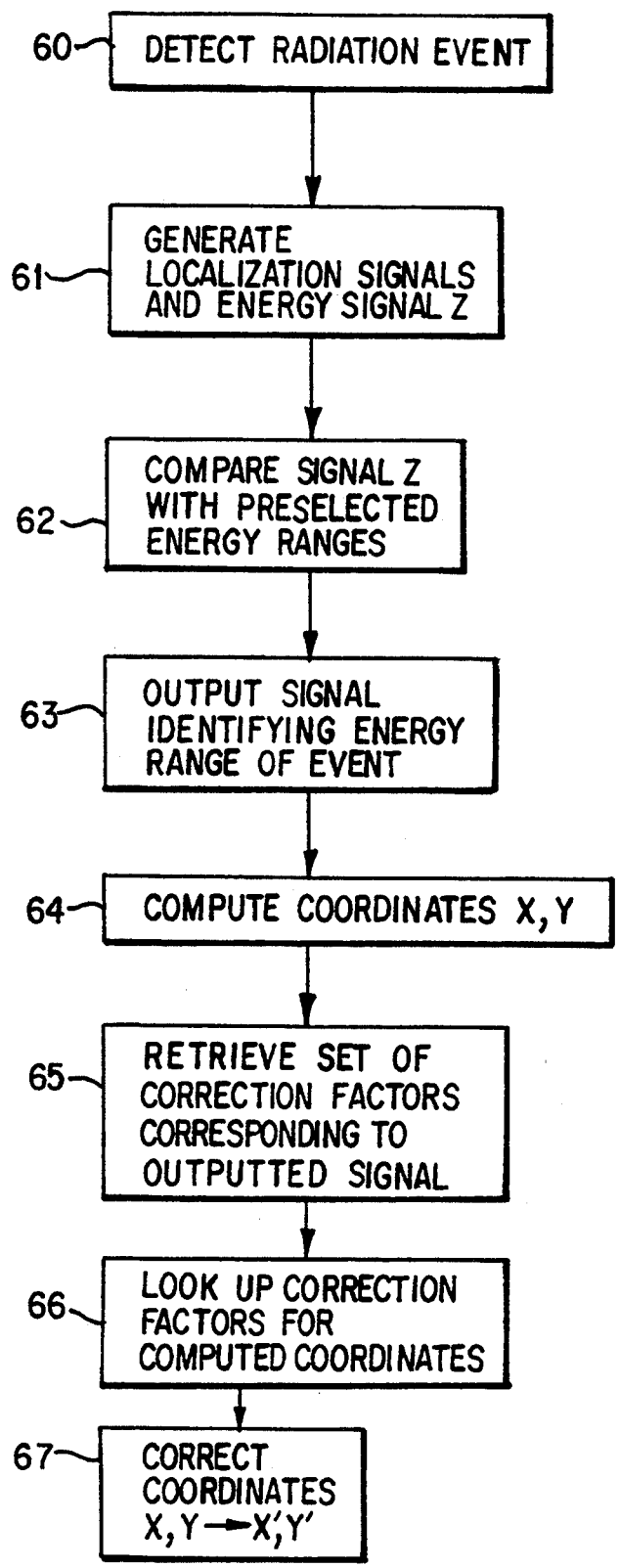
FIG. 4 is a flow chart diagram of one embodiment of the operation of the linearity correction procedure performed by the scintillation camera according to the present invention.

FIG. 4 is a flow chart describing the procedure for correcting the calculated spatial coordinates of a detected event according to its energy and position, as one embodiment of the invention. A radiation event is detected by camera head 10 at step 60. The localization signals X+, X−, Y+, Y− of the event and its energy signal Z are generated by the camera head 10 at step 61. At step 62, the energy signal Z is simultaneously compared with preselected different energy ranges in SCAs 41–43. At step 63, the SCA whose energy range corresponds to the inputted energy signal Z outputs a logic signal, identifying the energy range of the event whose calculated coordinates are input to the correction circuit 30, which logic signal is also inputted to the computing circuitry 20 via logic gate 44. At step 64, computing circuitry 20 computes the X, Y coordinates if a signal was received from gate 44. At step 65, the correction circuit 30 retrieves the appropriate set of correction factors corresponding to the outputted logic signal received from the SCAs. At step 66, the specific correction factors are looked up from the retrieved set for the particular X, Y coordinates, and at step 67 the looked up correction are used to correct the calculated coordinates X, Y to actual or true coordinates X', Y'.

The invention having been thus described, it will be obvious to those skilled in the art that the same may be varied in many ways without departing from the spirit and scope of the invention. Any and all such modifications are intended to be included within the scope of the following claims.

What is claimed is:

1. A method for correcting spatial coordinates of detected radiation events computed by a scintillation camera, comprising the steps of:
   determining the energy range of a detected radiation event;
   selecting a set of predetermined spatial coordinate correction factors as a function of the determined energy range of said detected event;
   retrieving correction factors from the selected set of predetermined spatial coordinate correction factors as a function of said computed spatial coordinates; and
   correcting said computed spatial coordinates with the retrieved correction factors.

2. A scintillation camera, comprising:
   a camera head including a detector for detecting an incident radiation event;
   means for computing spatial coordinates corresponding to the location of the detected radiation event;
   means for developing an energy signal proportional to the energy level of said detected radiation event;
   means for determining a range of energies into which said energy signal falls and generating a signal corresponding thereto;
   storage means for storing a plurality of sets of spatial coordinate correction factors, each corresponding to a particular energy range;
   means for selecting a set of spatial coordinate correction factors from said storage means as a function of said signal from said means for determining;
   means for retrieving correction factors from the selected set of spatial coordinate correction factors as a function of the computed spatial coordinates; and
   means for correcting said computed spatial coordinates with the retrieved correction factors.

3. A scintillation camera according to claim 2, wherein said means for determining a range of energies comprises a plurality of single channel analyzers, each being set to have upper and lower thresholds defining different energy ranges.

4. A method of calibrating a scintillation camera, comprising the steps of:
   obtaining separate sets of spatial coordinate correction factors for each of a plurality of radiation events of different energy ranges; and
   storing the separately obtained sets of spatial coordinate correction factors in a storage memory of said scintillation camera along with the energy range to which each of said sets corresponds.

5. The method of claim 4, wherein the step of obtaining comprises the steps of:
   for each different energy range, exposing said scintillation camera to a plurality of uniform parallel radiation lines of known coordinate values;
   accumulating detected radiation events generated by said plurality of radiation lines;
   calculating spatial coordinates for the detected radiation events;
   comparing the calculated spatial coordinates with said known coordinate values; and
   computing said spatial coordinate correction factors based on differences between said calculated spatial coordinates and said known coordinate values.

6. The method of claim 4, wherein the step of obtaining comprises the steps of:

exposing said scintillation camera to a plurality of uniform parallel radiation lines of known coordinate values and within a first energy range;

accumulating detected radiation events generated by said plurality of radiation lines;

calculating spatial coordinates for said detected radiation events;

comparing the calculated spatial coordinates with said known coordinate values;

computing a first set of spatial coordinate correction factors based on differences between said calculated spatial coordinates and said known coordinate values; and computing spatial coordinate correction factors for radiation events of a second energy range by extrapolation from said first set of spatial coordinate correction factors.

* * * * *